United States Patent [19]

Taylor

[11] Patent Number: 4,759,369
[45] Date of Patent: Jul. 26, 1988

[54] PULSE OXIMETER

[75] Inventor: Andrew C. Taylor, Whitland, Wales

[73] Assignee: Novametrix Medical Systems, Inc., Wallingford, Conn.

[21] Appl. No.: 882,726

[22] Filed: Jul. 7, 1986

[51] Int. Cl.$^4$ ............................. A61B 5/00; A61B 6/00
[52] U.S. Cl. ....................................... 128/633; 128/664; 128/666
[58] Field of Search ................. 128/633, 634, 664, 666

[56] References Cited

U.S. PATENT DOCUMENTS 4,586,513 5/1986 Hamaguri ........................... 128/633

FOREIGN PATENT DOCUMENTS 0102816 3/1984 European Pat. Off. ............ 128/633

Primary Examiner—Kyle L. Howell
Assistant Examiner—John C. Hanley
Attorney, Agent, or Firm—Howard F. Mandelbaum

[57] ABSTRACT

A pulse oximeter includes a capacitive d.c. blocking element to separate the time varying red and infra-red components of a light source transmitted through or reflected form the blood from the composite light signals. The magnitudes of the signal amplitudes are then digitized and converted for use as independent variables applied to a ROM based look-up table to determine blood oxygen saturation.

3 Claims, 3 Drawing Sheets

PULSE OXIMETER

BACKGROUND OF THE INVENTION

Pulse oximetry is a well known technique for non-invasive measurement of oxygen saturation in the blood of a living person. Generally pulse oximeters measure changes in the color of the arterial blood caused by changed in the ratio of hemoglobin and oxyhemoglobin present. The arterial blood is distinguished from venous blood and other tissue by its pulsatility.

Conventional pulse oximeters measure light transmittance through or reflectance from the blood at two wave lengths, e.g. red and infra-red. Measurements of the pulsatile and nonpulsatile components of the red and infra-red output signals are then processed using a relationship derived form the Lambert-Beers, law to compute oxygen saturation.

Some oximeters scale the magnitudes of the resultant signals making the non-pulsatile components equal so that the ratio of the pulsatile components relates directly to oxygen saturation. U.S. Pat. No. 4,407,290 to Wilbur for Blood Constituent Measuring Device and Method discloses an oximeter which scales the analog red and infra-red output signals so that their constant components are equal and then subtracts a d.c. voltage having a magnitude equal to that of the d.c. component. This enables the signals to be compared using the Lambert-Beers relationship with a simplified computation. However, the analog scaling and subtraction can provide a source of error because of limitations of the circuit and the Lambert-Beers computation, although simplified, is still complex to calculate.

Another approach, as exemplified by the pulse oximeter disclosed in European Patent Application No. 83304949.8, computes the ratios required for the Lambert-Beers relationship. A look-up table is used to apply the relationship without actually performing the mathematical manipulations required by Lambert-Beers. Although this method reduces computation time it is still prone to error resulting from deviations between empirical and theoretical factors.

SUMMARY OF THE INVENTION

In order to overcome the aforementioned shortcomings of prior art oximeters, the present invention teaches the use of a simplified oximeter design with improved accuracy and reduced calculation time. More specifically, the invention includes a pulse oximeter for measuring oxygen saturation in the blood of a person with means for directing light having a first wave length toward a tissue surface and the blood carried thereunder, means for directing light having a second wave length toward the tissue surface and the blood, and means for sensing the light of first and second wave lengths after its intensity has been affected by the color of the blood and for producing an electrical signal with a magnitude that is a function of the color of the blood and the pulse of the person, the signal being separable into a constant component and a pulsatile, i.e., time varying component, and means responsive to the electrical signals for determining a numerical measurement of oxygen saturation including charge storage means having an input terminal to which the electrical signal is applied and an output terminal at which there is produced an output signal having a waveform corresponding substantially to that of only the time varying component and substantially independent of the constant component, the determining means including memory means for storing representations of empirical numbers corresponding to predetermined oxygen saturation levels for comparison with Lambert-Beers ratios calculated from the pulsatile and composite electrical output signals and for calculating oxygen saturation levels as a function of the addresses of the empirical numbers in memory.

It is therefore an object of the invention to determine saturation by comparing the measured red and infra-red signal levels resulting from transmission of light through or reflection of light from blood with empirically derived data.

Another object of the invention is to make comparisons between the measured signal levels and empirical data more rapidly than computation of the Lambert-Beers formula.

Still another object of the invention is to provide a measure of oxygen saturation corrected for factors which cause deviations from the theoretical Lambert-Beers predictions, irrespective of whether the factors are identifiable.

A further object of the invention is to increase the accuracy of oxygen saturation measurements by updating the empirical relationship between blood measurements and oxygen saturation as it becomes better defined.

Other and further objects of the invention will be apparent from the following drawings and description of a preferred embodiment of the invention in which like reference numerals are used to indicate like parts in the various views.

DESCRIPTION OF THE PREFERRED EMBODIMENT

Figure 1:
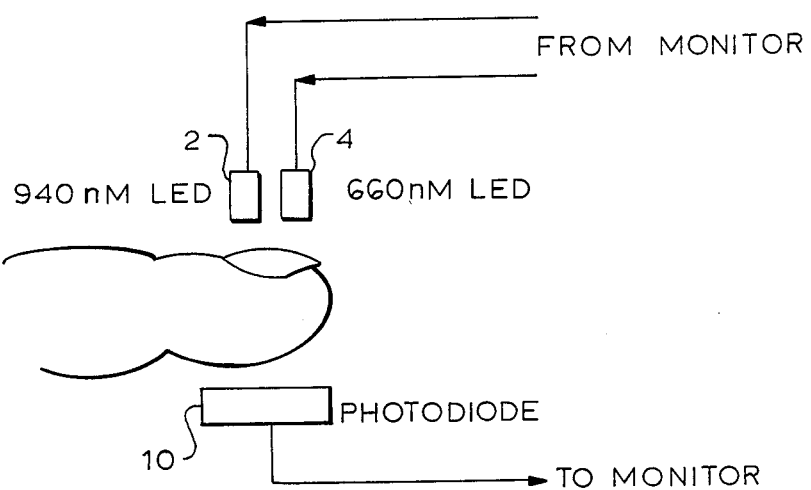
FIG. 1 is a schematic view of a part of the preferred embodiment of the invention in use in its intended environment.

Referring now to FIG. 1 of the drawings there is shown a sensor 2 (conventionally mounted in a housing not shown) which is adapted to be placed over the vascularized tissue of a patient, e.g., on a finger or ear lobe, whose hemoglobin oxygen saturation is to be measured. Mounted within the housing are two light emitting diodes (LEDs) 2 and 4 respectively. LED 2 emits light at a frequency of 660 nanometers and LED 4 emits light at a frequency of 940 nanometers. The light emitting surfaces of the LEDs 2 and 4 are directed at an opening in the housing in which the patient's vascularized tissue is received. A photodiode 10 is mounted on the opposite side of the housing with it slight sensitive surface orthogonal to the axis of maximum light emission from the LEDs, such that it receives light that has been transmitted through the tissue.

Figure 2:
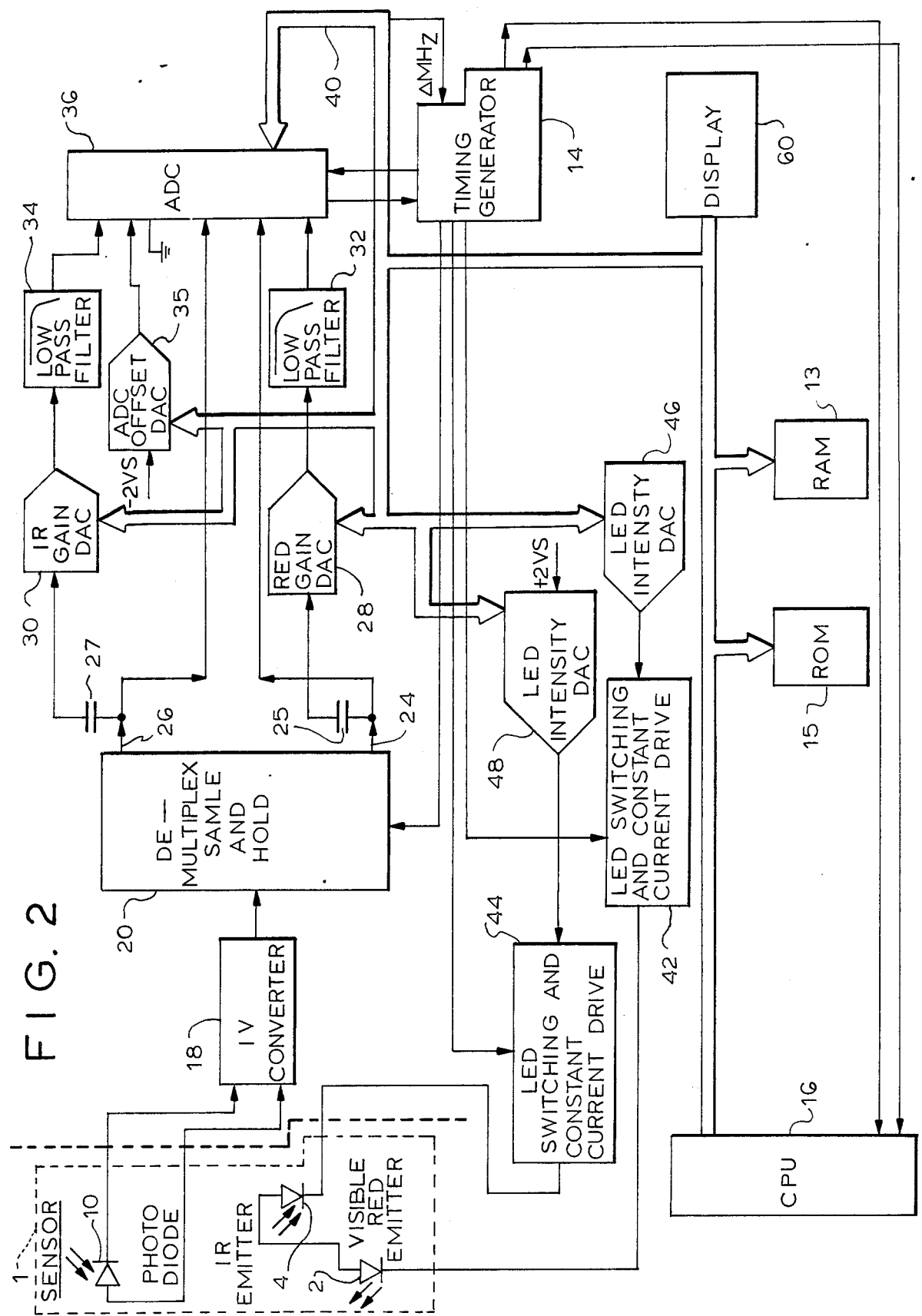
FIG. 2 is a schematic block diagram of the preferred embodiment of the invention.

Pulses are alternately applied to the LEDs 2 and 4 under the control of a microprocessor 16 of a digital computer 12 shown in FIG. 2. The computer 12 includes, in addition to the microprocessor 16, a random access memory (RAM) 13 and a read only memory (ROM) 15. In the ROM 15 there is stored a program for calculating the Lambert-Beers ratio from the respective amplitudes of the pulsatile and constant components of the measured light transmissions through the blood, as known in the art, but which does not perform the logarithmic computation required by the Lambert-Beers law. There is also stored, a table with addresses corresponding to predetermined oxygen saturation values and, for each, a corresponding number equal to he ratio that would be calculated from the red and infra-red signal outputs developed in the course of monitoring a patient whose oxygen saturation level was equal to the respective saturation value. Unlike oximeters which compute saturation from logarithmic formulas based on the classical Lambert-Beers relationship or their Taylor series approximations, in accordance with the invention saturation is determined by comparing the Lambert-Beers ratio calculated for the measured red and infrared signal levels with empirically derived data.

An area of the ROM 15 contains values of the empirically derived ratios with which the Lambert-Beers ratios derived from the pulsatile and constant component amplitudes are compared, in the form of the aforementioned table. In the preferred embodiment of the invention, the table contains only those empirically derived ratios which correspond to equally spaced discrete saturation levels. Saturation is calculated by comparing the value of the measured Lambert-Beers ratio with the values in the table until it is found to lie between two consecutive table values. Then the address of the match in the table gives the saturation value from the following formula which is simply calculated.

$$\text{Saturation \%} = 100 - \text{Address}_{min}$$

where $\text{Address}_{min}$ is the lower of the two addresses of the ratios between which the measured ratio lies.

For example, the table may appear as follows:

| Address | Lambert-Beers Ratio |
|---------|---------------------|
| 1 | R1 |
| 2 | R2 |
| 3 | R3 |
| 4 | R4 |
| 5 | R5 |
| . | . |
| . | . |
| . | . | where R1 is the ratio corresponding to a saturation level of 99.5%, R2 correspond to 98.5%, R3 corresponds to 97.5%, etc. If the measured ratio lies between R3 and R4, saturation is computed as $100 - 3 = 97\%$.

The integer result is sufficiently precise for most medical applications. Further precision can be obtained by using ratios corresponding to more closely spaced saturation levels in the table.

The foregoing approach provides the following benefits. Comparisons between the measured signal levels can be made more rapidly than the computations required by use of the Lambert-Beers relationship can be done. Hence an improvement in system computation time is achieved. Additionally, correction is made for factors which cause deviations from the theoretical Lambert-Beers predictions, even when the factors are not individually identifiable. Furthermore, as more is learned concerning the expected relationship between red and infra-red signal values and oxygen saturation and as more empirical data is analyzed, the saturation table can be updated by the mere expedient of replacing the ROM 15 with one containing the updated table. It is also possible to employ electrically erasable programmable read-only memories ($E^2$PROMS) to enable updating without ROM replacement.

A timing generator 14 is connected to an interrupt input of the microprocessor 16 and periodically applies interrupt signals to the microprocessor 16 to indicate that new data has been digitized and is available for input. The timing generator 14 is driven by a 4 MHz signal derived from the crystal clock oscillator output of the microprocessor 16. The timing signals for sequentially pulsing the LEDs 2 and 4 are derived by frequency dividers in the timing generator 14.

Constant current drive circuits 42 and 44 respectively connected to the cathodes of the respective LEDs 2 and 4, are turned on and off in response to application of the timing signals from the timing generator 14. When actuated by the timing signals from the timing generator 14, the constant current drive circuits 42 and 44 provide constant currents, the magnitudes of which depend on the amplitudes of the LED intensity signals generated by respective LED intensity signal generators 46 and 48.

The LED intensity signal generators 46 and 48 have respective digital inputs connected to the bus 40. In the event that the red and infra-red signal inputs to the analog to digital converter 36 are beyond the useful range of the A/D converter 36, e.g., due to skin thickness and pigment variations among subjects, the microprocessor responds by changing the level of the digital input signals to the LED intensity signal generators 46 and 48 thereby effecting the appropriate change in the level of the analog signals applied to the drive circuits 42 and 44.

Energizing signals are continuously applied to the LEDs 2 and 4 which are switched on and off under control of the microprocessor 16. In the preferred embodiment of the invention, enabling signals are sequentially applied to each of the LEDs every 640 microseconds, i.e. at 1.56 kHz as shown in FIG. 3 with the phase of the enabling pulses in the 940 nanometer channel being shifted with respect to the phase of the pulses in the 660 nanometer channel.

Figure 3:
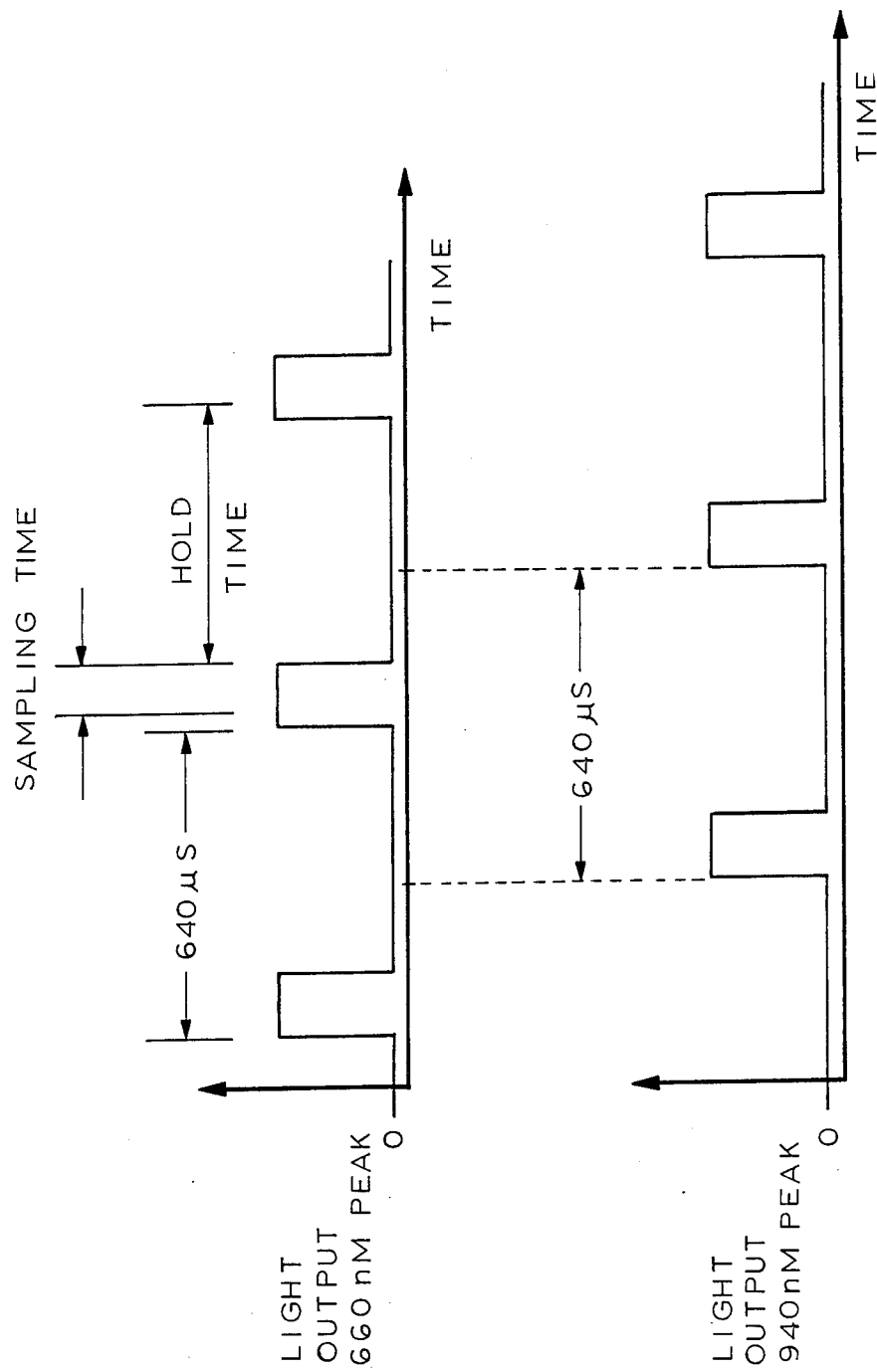
FIG. 3 is a timing diagram of some of the switching signals employed in the preferred embodiment of the invention.

As seen in FIG. 3, after each occurrence of a pulsing of the 940 nM channel followed by a pulsing of the 660 nM channel, storage of values is done by the microprocessor 16 as will be explained hereinafter.

The single photodiode 10 is employed to sense the light output of each of the LEDs 2 and 4 which is transmitted through the blood stream in the vascularized tissue. The current output of the photodiode 10 is applied to a current to voltage convert 18 which includes an operational amplifier having a high slewing rate characteristic and an output which is connected to a demultiplexer and sample and hold circuit 20. The current to voltage converter 18 and the circuitry to which it is connected, other than the LEDs 2 and 4, and photodiode 10, is housed in a monitor 22 so that the sensor 1 may be small, light in weight, and economically manufactured. The demultiplexer 20 separates and distributes the voltage output of the current to voltage converter 18, which consists of a pulse train having two sets of peaks, between two channels, 24 and 26, corresponding to the 660 nM and 940 nM signals, respectively.

Figure 4:
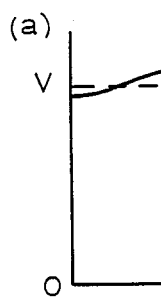
FIG. 4 is a graphic view of signals developed in the preferred embodiment of the invention.
Figure 4:
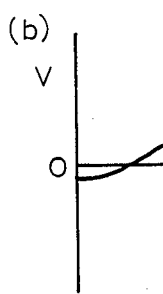
Figure 4:
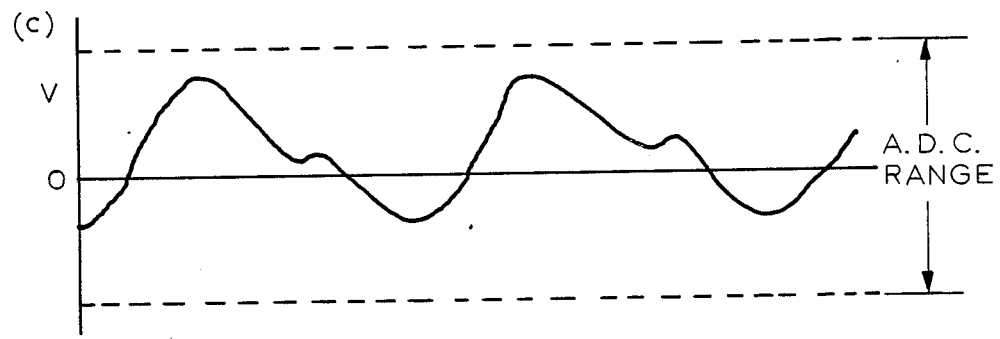

Each of the two channel outputs of the demultiplexer 20 is connected through a d.c. blocking capacitor 25, 27, to a respective amplifier 28, 30, the output of which is connected to a respective low pass filter 32, 34. The output signal from the demultiplexer 20 is shown in FIG. 4(a) without the effects of pulsing the LEDs 2 and 4. The waveform of the signals applied to the low pass filters 32, 34 is stepped and includes transients due to the switching of the demultiplexer 20. It is smoothed in the low pass filters 32, 34 wherein the high frequency transients are removed. The output of each of the amplifiers 28, 30 has a waveform as shown in FIG. 4(b) (ignoring the pulsing effects of the LEDs 2 and 4) which consists of an a.c. component superimposed on a zero d.c. level due to the blocking action of the capacitors 25 and 27. The magnitude of the D.C. level is a function of the intensity of the corresponding LED 2, 4, the sensitivity of the photodiode 10, the optical density of the tissue, and the mean volume of arterial blood, through which the light emitted by the LEDs must pass. The a.c. component has a frequency which varies with pulse rate and an amplitude which is a function of the change in volume of the arterial blood throughout the cardiac cycle, and the ratio of oxygenated to total blood hemoglobin, i.e. oxygen saturation.

An offset voltage generator 35 generates an analog offset voltage in response to a digital input from the computer 12 in order to allow the analog to digital converter 36 to operate with ground as the center point of the analog input voltages, i.e., the full waveform (negative and positive) of the variable component signal can be applied to the A/D converter 36 for deriving digital representations of the changes in light absorption of the blood at red and infra-red wave lengths. The value of the offset signal required to enable the analog to digital converter 36 to operate with ground as a center point is computed via the microprocessor 16 and a digital representation is applied to a corresponding digital input of the offset voltage generator 35. An analog offset signal having an amplitude corresponding to the digital offset signal is then applied to the analog to digital converter 36.

Respective 8 bit digital gain inputs in the amplifiers 28 and 30 periodically receive digital byte output from the microprocessor 16 which indicates the degree of correction needed to adjust the amplitude of the a.c. components at the outputs of the amplifiers 28, 30 to make optimum use of the dynamic range of the analog to digital converter 36 which is connected to a data input of the microprocessor 16. The gains of the amplifiers 28 and 30 are adjusted to a value approximately equal to two thirds ($\frac{2}{3}$) of the full dynamic range of the A/D converter 36. The amplified waveform at the output of the low pass filters 32 and 34 is of the form illustrated in FIG. 4(c). These waveforms are applied via bus 40 to the A/D converter 36 and the digital output thereof is applied to a data input of the microprocessor 16. The A/D converter 36 is operated to bipolar mode thereby enabling the full pulse waveform at the output of low pass filters 32 and 34 to be tracked.

For each output pulse appearing at the output of low pass filters 32 and 34 and digitized in the A/D converter 36, the voltage sample is tested to determine if it is a maximum or peak voltage. Detection of the peaks and troughs of the red and infra-red variable signal components is also done by the microprocessor. Various peak and trough detection algorithms known to those skilled in the art may be employed to derive the maxima and minima of each cycle of the pulsatile variable components, and their difference which is digitized to represent the measurement of the variable components.

In addition to testing each voltage pulse at the output of low pass filters 32 and 34 to determine whether or not it is a peak, a similar test is made to determine whether a trough in the signal waveform has been reached. The peak to trough value of each cycle of the a.c. output signals from the low pass filters 32 and 34 are also utilized in the derivation of oxygen saturation.

After each pulse is applied to the A/D converter 36, it is tested for validity so that spurious signals due to artifact can be suppressed. Two tests are made. First the elapsed time between each pulse and the preceding one is compared to a predetermined minimum time corresponding to a maximum anticipated pulse rate. In the preferred embodiment of the invention, a maximum pulse rate of 250 beats per minute is used to derive a predetermined minimum time of 240 milliseconds between pulses. The second test involves a comparison of the pulse period with the previous pulse period to determine if excessive variability exists, in which case the pulse is rejected.

The analog to digital converter 36 receives the output signal from the low pass filters 32 and 34 which represent the amplitudes of the variable components of the red and infra-red signals, respectively (see FIG. 4(c)), and the output signals from the demultiplexer 20 which represent the amplitudes of the constant components of the red and infra-red signals, respectively (see FIG. 4(a)). The amplitudes are digitized in the analog to digital converter 36 and applied via bus 40 to the microprocessor 16 of the computer 12.

The amplitudes of the digitized signals are converted to suitable form for use with the look-up table stored in the ROM 15. The corresponding oxygen saturation measurement is then displayed on a conventional liquid crystal seven-segment numerical display 60.

It is to be understood and appreciated that alterations, modifications and variations of and to the preferred embodiment described herein may be made without departing from the spirit and scope of the invention which is defined in the following claims.

What is claimed is:

1. In a pulse oximeter for measuring oxygen saturation in the blood of a person comprising means for directing light having a first wave length toward a tissue surface and the blood carried thereunder; means for directing light having a second wave length toward said tissue surface and said blood; and means for sensing said light of first and second wave lengths after its intensity has been affected by the color of the blood and for producing an electrical signal with a magnitude that is a function of the color of the blood and the pulse of said person, said signal being separable into a constant component and a time varying component; and means responsive to said electrical signal for determining a numerical measurement of oxygen saturation, the improvement comprising:

charge storage means for blocking said electrical signal constant component and having an input terminal to which said electrical signal is applied and an output terminal at which there is produced an output signal having a wave form corresponding substantially to that of only said time varying component and substantially independent of said constant component;

first calculating means operatively connected to said charge storage means and to said sensing means for calculating a ratio as a function of said time varying component and constant component, said determining means including memory means having stored therein at assigned addresses ratios corresponding to predetermined oxygen saturation levels, and second calculating means operatively connected to said first calculating means for calculating oxygen saturation as a function of the address in said memory means having a stored ratio with a predetermined relationship to said calculated ratio.

2. A pulse oximeter according to claim 1 wherein said read only memory is erasable and programmable.

3. A pulse oximeter according to claim 1 wherein said charge storage means comprises a capacitor.

* * * * *

UNITED STATES PATENT OFFICE
CERTIFICATE OF CORRECTION

Patent No. 4,759,369        Dated Jul. 26, 1988

Inventor(s) Andrew C. Taylor

It is certified that error appears in the above-identified patent and that said Letters Patent are hereby corrected as shown below:

At column 1, line 9 change "changed" to --changes--.

At column 1, line 36, change "83304949.8" to --83304939.8--.

At column 3, line 51, change "correspond" to --corresponds--.

At column 5, line 5, change "to" to --in--.

Signed and Sealed this

Sixth Day of December, 1988

Attest:

DONALD J. QUIGG

*Attesting Officer*        *Commissioner of Patents and Trademarks*